(12) United States Patent
Judell

(10) Patent No.: US 7,302,360 B2
(45) Date of Patent: Nov. 27, 2007

(54) DEFECT SIZE PROJECTION

(75) Inventor: Neil Judell, Newtonville, MA (US)

(73) Assignee: Ade Corporation, Westwood, MA (US)

( * ) Notice: Subject to any disclaimer, the term of this patent is extended or adjusted under 35 U.S.C. 154(b) by 26 days.

(21) Appl. No.: 11/321,689

(22) Filed: Dec. 29, 2005

(65) Prior Publication Data

US 2006/0178855 A1    Aug. 10, 2006

Related U.S. Application Data

(63) Continuation-in-part of application No. 10/971,694, filed on Oct. 22, 2004, now Pat. No. 7,184,928.

(60) Provisional application No. 60/514,289, filed on Oct. 24, 2003.

(51) Int. Cl.
*G01N 21/88*    (2006.01)

(52) U.S. Cl. .................. 702/166; 356/237; 356/343; 356/446; 356/371; 356/342

(58) Field of Classification Search ............... 702/166; 356/237, 601
See application file for complete search history.

(56) References Cited

U.S. PATENT DOCUMENTS 5,712,701 A * 1/1998 Clementi et al. ......... 356/237.2
2003/0058455 A1   3/2003 Ebihara et al. ............. 356/601

* cited by examiner

*Primary Examiner*—John Barlow
*Assistant Examiner*—Sujoy Kundu
(74) *Attorney, Agent, or Firm*—Weingarten, Schurgin, Gagnebin & Lebovici LLP

(57) ABSTRACT

A system and method of inspecting semiconductor wafers that is capable of determining a scattering power associated with a wafer surface defect whether or not the scattering power associated with the defect exceeds the dynamic range of the system. The scattering power of the detected defect is obtained by determining the height of a Gaussian shape representing data collected by the system. The height of the Gaussian shape may be determined by defining a cross-sectional area of the Gaussian shape at an intermediate height, determining a cross-sectional area value and combining the area value, intermediate height and a slope value m that is representative of a relationship between the area of a cross-section in a Gaussian pulse and the height of the pulse at the cross-section. The technique increases the dynamic range of the equipment with a uniform scan process that can determine all defect sizes in a single scan pass.

18 Claims, 5 Drawing Sheets

DEFECT SIZE PROJECTION

CROSS REFERENCE TO RELATED APPLICATIONS

This is a Continuation-in-Part application of U.S. patent application Ser. No. 10/971,694, filed Oct. 22, 2004 now U.S. Pat. No. 7,184,928 entitled EXTENDED DEFECT SIZING, which claims benefit of U.S. Provisional Patent Application No. 60/514,289, filed Oct. 24, 2003, entitled EXTENDED DEFECT SIZING.

STATEMENT REGARDING FEDERALLY SPONSORED RESEARCH OR DEVELOPMENT

N/A

BACKGROUND OF THE INVENTION

1. Field of Invention

The present invention relates generally to systems and methods of inspecting semiconductor wafers, and relates more specifically to a semiconductor wafer inspection system and method capable of detecting and measuring wafer defects in which the scattering power of the defect exceeds the dynamic range of the system.

2. Description of Related Art

Systems and methods of inspecting semiconductor wafers are known for detecting and measuring defects occurring on a surface of a semiconductor wafer. For example, a conventional laser-based surface scanning inspection system is typically configured to detect localized light scatters on a semiconductor wafer surface. Such localized light scatters may be indicative of one or more defects on the wafer surface that may render an integrated circuit(s) (IC) fabricated on the wafer to be inoperative. In a typical mode of operation, the conventional surface scanning inspection system sweeps a laser light beam in a predetermined direction, while the wafer being inspected rotates under the swept beam at an angle of about 90° to the predetermined sweep direction. Next, the conventional surface scanning inspection system detects a light beam reflected from the wafer surface, and samples the detected signal in both the predetermined direction of the swept beam and in the direction of rotation to obtain a two-dimensional array of data. When the light beam sweeps over a defect on the wafer surface, the data obtained by the wafer inspection system generally corresponds to the beam shape of the laser spot power at the wafer surface. This is because such wafer surface defects are generally much smaller than the spot size of the laser beam. After the conventional surface scanning inspection system has detected a defect, the system may attempt to measure the size of the defect by determining the value of the maximum scattering power of the defect, and may also determine the location of the defect on the surface of the wafer.

One drawback of the above-described conventional laser-based surface scanning inspection system is that the maximum scattering power of a detected defect may exceed the dynamic range of the system. As a result, the electronics within the wafer inspection system may saturate, thereby causing at least some of the defect size measurements performed by the system to be at a power level at which the measurements become nonlinear due to the saturation effects.

One way of addressing the effects of saturation on defect size measurements made by the conventional laser-based surface scanning inspection system is to employ a data extrapolation technique. However, such data extrapolation techniques are often difficult to perform in conventional wafer inspection systems. Alternatively, the conventional surface scanning inspection system may perform a nonlinear least squares fit of the measurements to a given Gaussian shape, which may be characterized by a number of parameters including an estimated amplitude, an estimated inverse correlation matrix, and an estimated pulse center location. However, conventional algorithms for performing such nonlinear least squares fit techniques often require a significant amount of processing time. Further, relatively small changes in the data resulting from, e.g., noise or a non-ideal signal, may lead to significantly large changes in the estimated parameters.

One methodology that takes advantage of pulse cross-section area and height to predict pulse height has been employed to handle very large defects. For these large defects, the area of the defect where the equivalent voltage is larger than a set-point threshold is measured. The methodology uses an empirical calibration between area and particle size, and has proven to be quite robust. There is a drawback to the methodology in that it adds some difficulty because it uses a completely separate calibration process, which can be time consuming and cumbersome.

It would therefore be desirable to have an improved system and method of inspecting semiconductor wafers that can measure the size and determine the location of a defect on a surface of a semiconductor wafer while avoiding the drawbacks of conventional wafer inspection systems and methods.

BRIEF SUMMARY OF THE INVENTION

In accordance with the present invention, a system and method of inspecting semiconductor wafers is provided to determine size and location of wafer defects over a wide dynamic range of observation using two defect size estimation techniques. The system and method develops an equivalent voltage or power value for a defect related to defect size, which is compared against theoretical models or empirical calibration data to determine the defect sizing. The system and method of the present invention derives information about at least one aspect of a defect from a first defect size estimation technique for predicting defect sizing over a first defect size range, and incorporates the information into a second defect size estimation technique for predicting defect size over a second defect size range.

In one embodiment, the first methodology uses a plurality of cross-sections of a Gaussian pulse representative of the defect, curve fitting and knowledge of the beam shape to determine the voltage equivalent magnitude of a defect, and the second methodology combines a slope value representative of a relationship between the area of a cross-section in a Gaussian pulse and the height of the pulse at the cross-section, a predetermined voltage threshold, and an estimate of a defect area at the predetermined voltage threshold, to determine the voltage equivalent magnitude of a defect.

The system and method according to the present invention provides a unified method for sizing defects that extend an accurate dynamic range of the system significantly. The two different defect-sizing techniques develop equivalent voltage or power values related to defect size over potentially different defect size ranges.

According to an aspect of the present invention, a slope value that is representative of a relationship between the area of a cross-section in a Gaussian pulse and the height of the pulse at the cross-section is obtained according to a first defect size estimation technique. The slope value is applied to a second defect size estimation technique for determining an equivalent voltage for a Gaussian pulse and thus a defect amplitude in large size defects. The slope value comprises a system slope value that is based on known characteristics of the defect inspection system such as spot size of a system laser beam. Alternatively, it comprises a measured slope value that is based on the above-described relationship and is computed from data representative of an area of at least one cross-section in a Gaussian pulse at a selected height.

According to another aspect of the present invention, an equivalent voltage for a large single defect may be generated by combining the slope value, a predetermined voltage threshold, and an estimate of a defect area at the predetermined voltage threshold. In an illustrative but not necessarily preferred embodiment, the predetermined voltage threshold is an unsaturated voltage threshold. In an illustrative but not necessarily preferred embodiment, the slope value is derived from information taken from another technique for obtaining equivalent voltages for sizing defects and based on Gaussian pulse estimates. The combination of the two defect sizing techniques permits a uniform process to be applied to all defects on a wafer, even when the unsaturated range of the equipment is exceeded. According to an advantage of the present invention, the uniform process obtains equivalent voltages for large size defects. The process can provide sizing for defects directly from voltage associated with the scattering power of the defect over two different defect size ranges. According to another advantage of the present invention, defect sizing determinations can be obtained in a single scan of the wafer. This advantage permits accurate measurements of defects that differ in size by many orders of magnitude without recalibration of the system.

In accordance with an embodiment of the present invention, a system and method of inspecting semiconductor wafers is provided that is capable of measuring the size and determining the location of a wafer surface defect whether or not the scattering power associated with the defect exceeds the unsaturated range of the system. The semiconductor wafer inspection system includes an optical module including a surface scanning mechanism and a light channel (LC) detector including LC optics. In an illustrative but not necessarily preferred embodiment, the surface scanning mechanism is an acousto-optic deflector (AOD), and the LC optics comprises a quadcell photodetector. The AOD is configured to emit at least one collimated beam of laser light toward a surface of a semiconductor wafer at an oblique angle of incidence $\theta_i$. The LC optics are configured to detect a light beam specularly reflected from the wafer surface at an angle of reflection $\theta_r$.

According to a disclosed embodiment, the size of a defect detected on a semiconductor wafer surface using the surface scanning laser beam is obtained by determining the height of a Gaussian shape representing data collected by the wafer inspection system. The height of a geometric Gaussian shape in three dimensional space is determined by defining an intermediate height of the Gaussian shape, obtaining the cross-sectional area of the Gaussian shape at the intermediate height, determining a value of the cross-sectional area, and combining the cross-sectional area value with a slope value in a predetermined relationship to obtain an equivalent voltage value for the defect. The slope value comprises the slope of a linear relationship between cross-sectional areas of a Gaussian pulse and the natural log of the voltage heights of the pulse at the cross sections. An equivalent voltage amplitude of a large defect can thus be calculated using a relationship between a cross-sectional area at a predetermined cut height, also known here as a height threshold, the height threshold itself, and the slope value. The equivalent voltage amplitude so calculated provides greater accuracy for large defects than a slope estimation technique or the use of the relationship between area at a height threshold and peak voltage or power by themselves.

According to a feature of the present invention, defect sizing estimates based on three-dimensional Gaussian pulses can be obtained using knowledge of a shape of a beam directed at a wafer and curve fitting techniques to determine a voltage or power equivalent magnitude of a defect. The voltage equivalent magnitude is converted to scattered power produced by the incident beam and then to defect size. When the defect size is very large, the linear relationships relied on can change to include non-linear elements, compromising the accuracy of the technique. When nonlinearities are introduced, such as when non-Gaussian elements and terms become significant in the calculation, an additional technique is used to improve the accuracy of the defect detection, which includes measuring an area of a pulse generated from a defect that has a voltage or power level greater than a predetermined threshold set point. An equivalent power or voltage amplitude is calculated by measuring an area of the pulse at the predetermined threshold set-point. The area is then combined with information based on the slope of a linear relationship between a cross-sectional area of a Gaussian pulse at a predetermined height, and the natural log of the height. The resulting equivalent voltage or power for the defect can then be converted to scattered power, and then defect size to determine the size of the large defect.

According to another embodiment of the present invention, a method of obtaining the size of a defect detected on a semiconductor wafer surface using the surface scanning laser beam includes determining a slope value m related to the slope of a linear relationship between cross-section area and the natural log of the height of the cross-section in a Gaussian pulse. The slope value m may be a system slope value M that is based in an exemplary embodiment on known characteristics of the defect inspection system such as a spot size of a system laser beam. For example, M can be derived in a system calibration in which $$M = \pi |R|^{\frac{1}{2}},$$

where R is a positive definite symmetric matrix describing a shape associated with the laser beam. Alternately, or in addition, the slope value may be a measured slope value M that is determined from data representative of area of at least one cross-section in a Gaussian pulse at a selected height and based on the linear relationship between a cross-sectional area and a natural logarithm of a value of a height substantially in accordance with the equation $$\text{Area} = \pi |R|^{\frac{1}{2}} (\ln(P_0) - \ln(\text{height})),$$

in which "$P_0$" is a maximum scattering power associated with the detected defect, and "R" is a positive definite symmetric matrix describing a shape associated with the laser beam. Upon determination of the slope value m, a predetermined voltage or power threshold and the area of the pulse cross-section at the threshold height are obtained. The threshold height and area are not necessarily correlated to the linear relationship that would be determined in the technique described above, due to the non-linear elements that are introduced with very large defects. An equivalent voltage or power for the defect that can represent defect amplitude can then be calculated based on the relationship given by the equation $$\text{Amplitude} = \text{threshold} * e^{(area/m)}$$

where threshold is the predetermined threshold height, area is the cross sectional area of the pulse at the threshold height, and m represents the slope value.

In accordance with the present invention, two methodologies are combined to predict an accurate pulse height and thus a defect size, without a separate calibration process for the measurement of large defects. According to another aspect of the invention, a system for determining a height of a geometric Gaussian shape in three dimensional space that is representative of a defect size on a wafer, comprises a data capture component for capturing data samples related to scattering power of an incident beam on a surface of the wafer; a processing engine for executing a set of instructions for analyzing the data samples and determining the height; and a code segment in the set of instructions for determining the height when the Gaussian shape exceeds a dynamic range of the equipment. The code segment is executable by the processing engine to determine a value representative of voltage or power amplitude substantially according to the equation $$\text{Amplitude} = \text{height} * e^{(area/m)}$$

where height is the intermediate height, area is the cross-sectional area value and m is a slope value that is representative of a relationship between an area of a cross-section in a Gaussian pulse and a height of the pulse at the cross-section.

Other features, functions, and aspects of the invention will be evident from the Detailed Description of the Invention that follows.

BRIEF DESCRIPTION OF THE SEVERAL VIEWS OF THE DRAWINGS

The invention will be more fully understood with reference to the following Detailed Description of the Invention in conjunction with the drawings of which.

DETAILED DESCRIPTION OF THE INVENTION

U.S. Provisional Patent Application No. 60/514,289 filed Oct. 24, 2003 entitled EXTENDED DEFECT SIZING and U.S. patent application Ser. No. 10/971,694 filed Oct. 22, 2004 of the same title are hereby incorporated herein by reference.

A system and method of inspecting a semiconductor wafer is disclosed that is capable of measuring the size and determining the location of a defect on a surface of a semiconductor wafer. The presently disclosed wafer inspection system can perform such sizing and locating of wafer surface defects whether or not the scattering power associated with the defect exceeds the dynamic range of the system.

Figure 1:
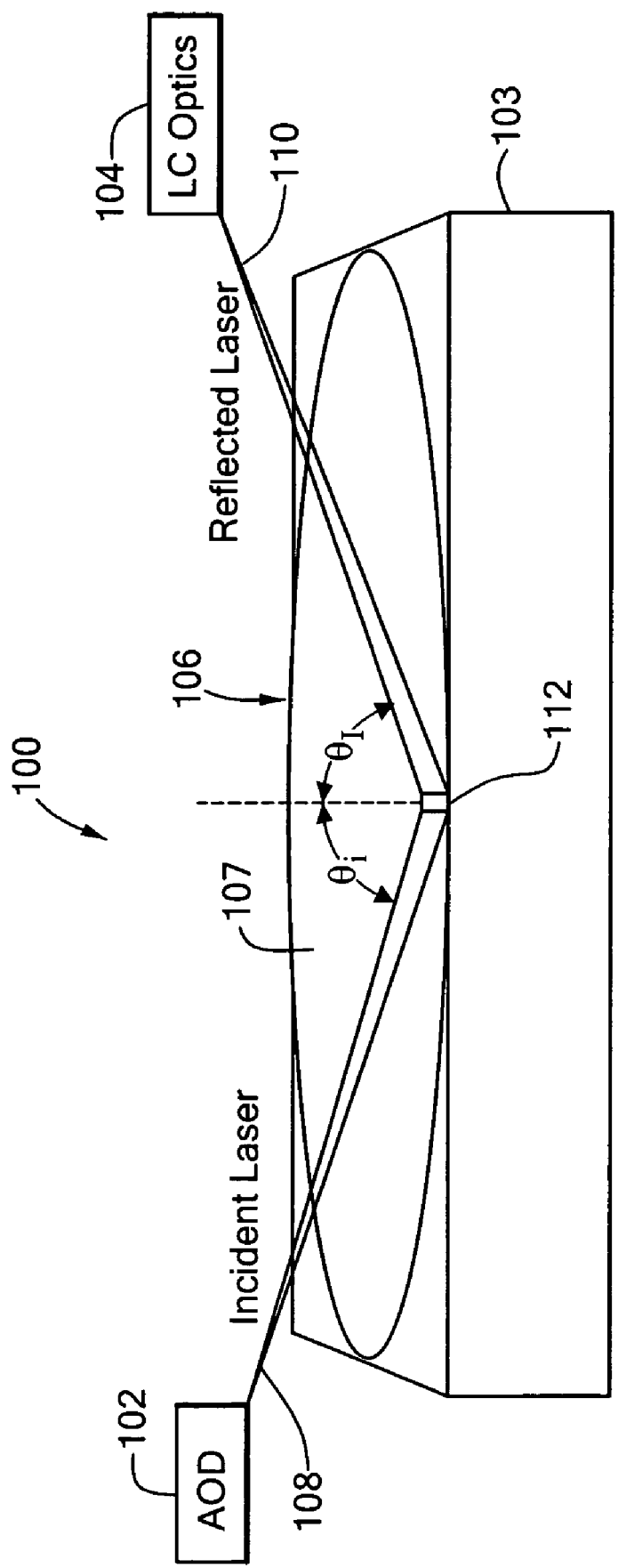
FIG. 1 is a block diagram of a laser-based wafer surface scanning inspection system according to the present invention, in which the system performs a scan of a laser beam on a surface of a semiconductor wafer to detect defects on the wafer surface.

FIG. 1 depicts an illustrative embodiment of a laser-based wafer surface scanning inspection system 100, in accordance with the present invention. In the illustrated embodiment, the surface scanning inspection system 100 comprises an optical module including a surface scanning mechanism 102, and a light channel (LC) detector including LC optics 104. For example, the surface scanning mechanism 102 may be an acousto-optic deflector (AOD) or any other suitable surface scanning mechanism, and the LC optics 102 may comprise a quadcell photodetector or any other suitable light detector. As shown in FIG. 1, the AOD 102 is configured to emit at least one collimated beam of laser light 108 toward a surface 107 of a semiconductor wafer 106 at an oblique angle of incidence $\theta_i$. Further, the LC optics 104 is configured to detect a light beam 110 specularly reflected from the wafer surface 107 at an angle of reflection $\theta_r$. Specifically, the LC optics 104 is configured to detect specular distortions in the reflected light beam 110. It is noted that the wafer 106 may also be inspected from the backside by inverting the wafer in the surface scanning inspection system 100.

For example, the AOD 102 may include a solid state laser such as a 532 nm wavelength diode-pulsed solid state laser, or any other suitable type of laser. In the illustrative but not necessarily preferred embodiment, the AOD 102 emits the laser light beam 108 to produce a focused laser spot having a diameter of about 30 microns for scanning the wafer surface 107, in which the incident angle $\theta_i$ of the emitted light beam 108 is about 65 degrees. It should be understood that the laser light beam 108 may alternatively be emitted by the AOD 102 at any suitable angle of incidence to produce any suitable spot size on the wafer surface. The surface scanning inspection system 100 further includes a theta stage 103 upon which the wafer 106 is held during inspection. The theta stage 103 is configured to rotate and to translate the wafer 106 through a scan line 112 produced by the AOD 102, thereby generating a spiral pattern of light used to inspect the wafer surface 107. The theta stage 103 includes an encoder such as an optical encoder that provides counts indicative of the rotational position of the stage 103 relative to a predetermined reference point. It is noted that the structure and operation of the theta stage 103 are known to those skilled in this art and therefore need not be described in detail herein.

Figure 2:
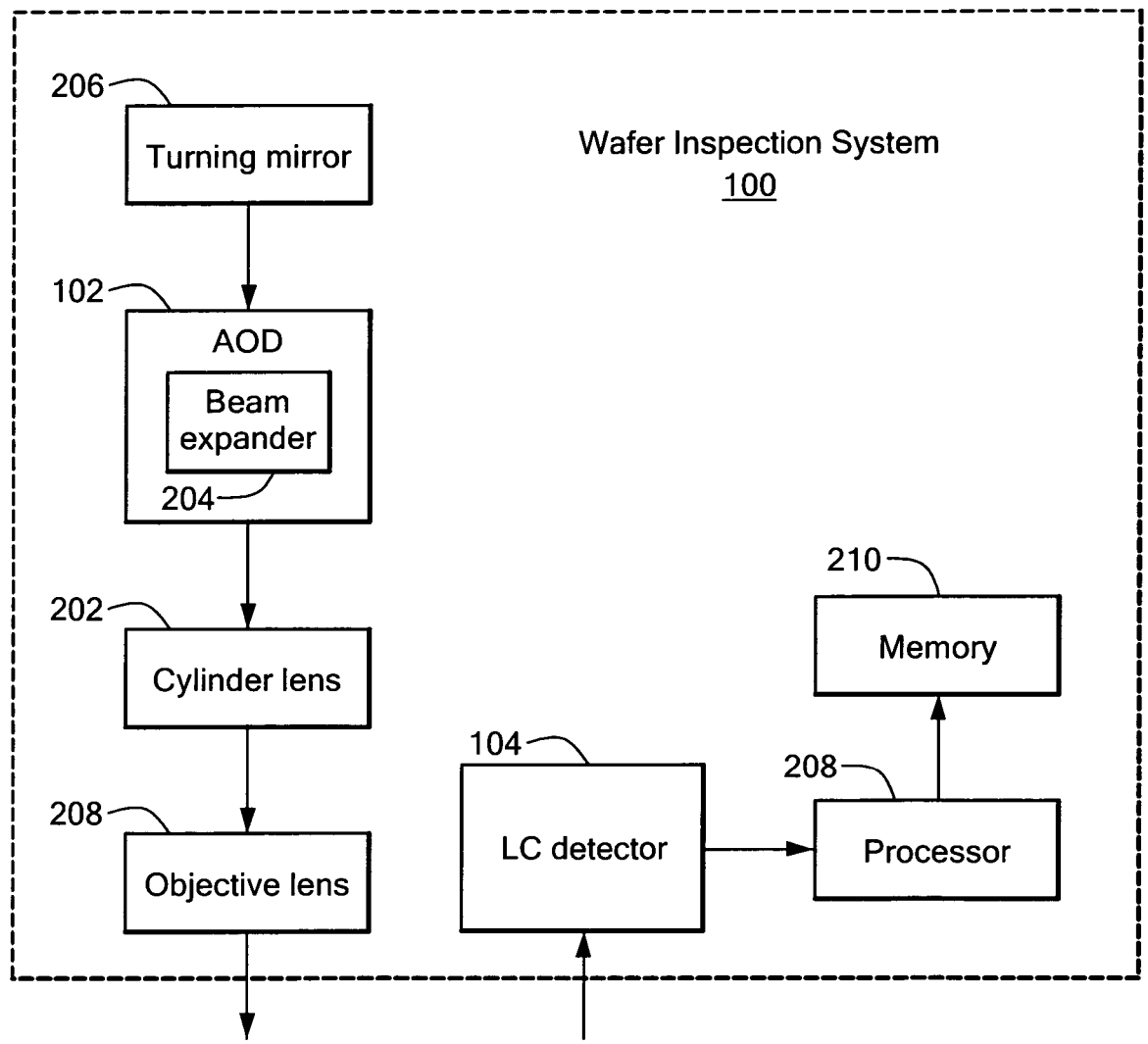
FIG. 2 is a functional illustration of components included in the surface scanning inspection system of FIG. 1.

FIG. 2 depicts a plurality of functional components included in the above-described surface scanning inspection system 100 (see FIG. 1). As shown in FIG. 2, the surface scanning inspection system shown as Wafer Inspection System 100 in FIG. 2, comprises a turning mirror 206, the AOD 102 including a beam expander 204, a cylinder lens 202, an objective lens 208, the LC optics 104, and a processor 208 and associated memory 210. In the illustrated embodiment, the AOD 102 is configured to generate the narrow angle light beam 108 by exciting a crystal with a high frequency sound wave. The beam expander 204 is configured to expand the light beam 108 before the beam enters an aperture of the AOD 102 to obtain a desired angle of deflection. The cylinder lens 202 is disposed at the output of the AOD 102, and is configured to compensate for parasitic cylinder lens loss that may be induced by the deflector. The scan is relayed through the objective lens 208 to the surface 107 of the wafer 106 (see also FIG. 1). The LC optics 104 is configured to receive the reflected light beam 110, and to detect any losses in light intensity resulting from specular distortion or deflection of the light beam 110.

In the illustrative but not necessarily preferred mode of operation, the surface scanning inspection system 100 (see FIG. 1) is configured to detect localized light scatters on the surface 107 of the wafer 106. For example, such localized light scatters may be indicative of one or more defects on the wafer surface 107 that may render an integrated circuit(s) (IC) fabricated on the wafer 106 to be inoperative. Specifically, the AOD 102 emits the laser light beam 108 toward the wafer surface 107 at the angle of incidence $\theta_i$ and sweeps the light beam 108 in a predetermined radial direction, while the theta stage 103 rotates under the swept beam 108 at an angle of about 90° to the predetermined radial direction. Next, the LC optics 104 detects the laser light beam 110 reflected from the wafer surface 107 at the angle of reflection $\theta_r$, and samples the detected signal in both the radial and rotational directions to obtain a two-dimensional array of data. It is noted that the sampling of the data is generally non-orthogonal. The processor 208 included in the surface scanning inspection system 100 is operative to process the sampled data by executing one or more programs out of its associated memory 210 (see FIG. 2).

In the presently disclosed embodiment, the corresponding location of each data sample on the wafer surface 107 is expressed as $$x_{in,xs}, y_{in,xs}, \tag{1}$$

in which the index "in" designates samples in the radial or "in scan" direction, and the index "xs" designates samples in the tangential or "cross scan" direction.

When the light beam 108 sweeps over a defect on the wafer surface 107, the data samples obtained by the surface scanning inspection system 100 generally correspond to the beam shape of the laser spot on the surface 107. This is because wafer surface defects are normally much smaller than the spot size of the laser beam 108. For example, the data samples may be represented by a geometric Gaussian shape that is non-isotropic due to the angle of incidence θi and the non-orthogonal sampling of the data.

The locations ($x_{in,xs}$, $y_{in,xs}$) of the data samples on the wafer surface 107 may be expressed as a column vector, i.e., $$\vec{z} = \begin{bmatrix} x_{in,xs} \\ y_{in,xs} \end{bmatrix}. \tag{2}$$

Accordingly, the optical laser spot power at the wafer surface 107 may be expressed as $$\text{power}(\vec{z}) = P_0 \exp(-(\vec{z} - \vec{z}_0)^t R^{-1} (\vec{z} - \vec{z}_0)), \tag{3}$$

in which "$P_0$" is the maximum scattering power of the defect, "$\vec{z}_0$" denotes the location of the defect, and "R" is a positive definite symmetric matrix describing the beam shape.

For example, if a laser spot is a Gaussian with a density of density(x)=$e^{-x^2/2\sigma^2}$, then the $1/e^2$ full-width may be expressed as 4σ. For an illustrative 50 micron $1/e^2$ full-width beam, which strikes a wafer at a 65-degree incident angle, then the density at the wafer surface may be expressed as $$\text{density}(x,y) = e^{-x^2/2(12.5\mu)^2} e^{-y^2/2(12.5\mu/\cos(65°))^2}. \tag{4}$$

Equation (4) above may be rewritten as $$\text{density}(x, y) = \exp \left( \begin{bmatrix} x \\ y \end{bmatrix}^t \begin{bmatrix} (12.5\mu)^2 & 0 \\ 0 & (12.5\mu/\cos(65°))^2 \end{bmatrix}^{-1} \begin{bmatrix} x \\ y \end{bmatrix} \right). \tag{5}$$

Accordingly, for this illustrative example, $$R = \begin{bmatrix} (12.5\mu)^2 & 0 \\ 0 & (12.5\mu/\cos(65°))^2 \end{bmatrix}. \tag{6}$$

In the event the sampled data comprises non-saturated data (i.e., the data sampling is linear), the surface scanning inspection system 100 may determine the value of $P_0$ in equation (3) above by identifying the largest value in the collection of measured data points, which may be expressed as $$\text{power}(x_{in,xs}, y_{in,xs}). \tag{7}$$

However, this technique for determining the value of $P_0$ generally does not yield useful results when the maximum scattering power of a detected defect exceeds the dynamic range of the surface scanning inspection system 100, i.e., when the sampled data comprises saturated data. As a result, at least some of the defect size measurements performed by the wafer inspection system may be at a power level at which the measurements become nonlinear due to the saturation effects.

According to the present invention, a technique is provided for measuring the size and determining the location of a defect on a surface of a semiconductor wafer when the maximum scattering power of a detected defect exceeds the dynamic range of the surface scanning inspection system 100, i.e., the sampled data collected by the wafer inspection system comprises saturated data. It is noted that the disclosed technique may be employed in the voltage domain for sizing wafer defects.

Figure 3:
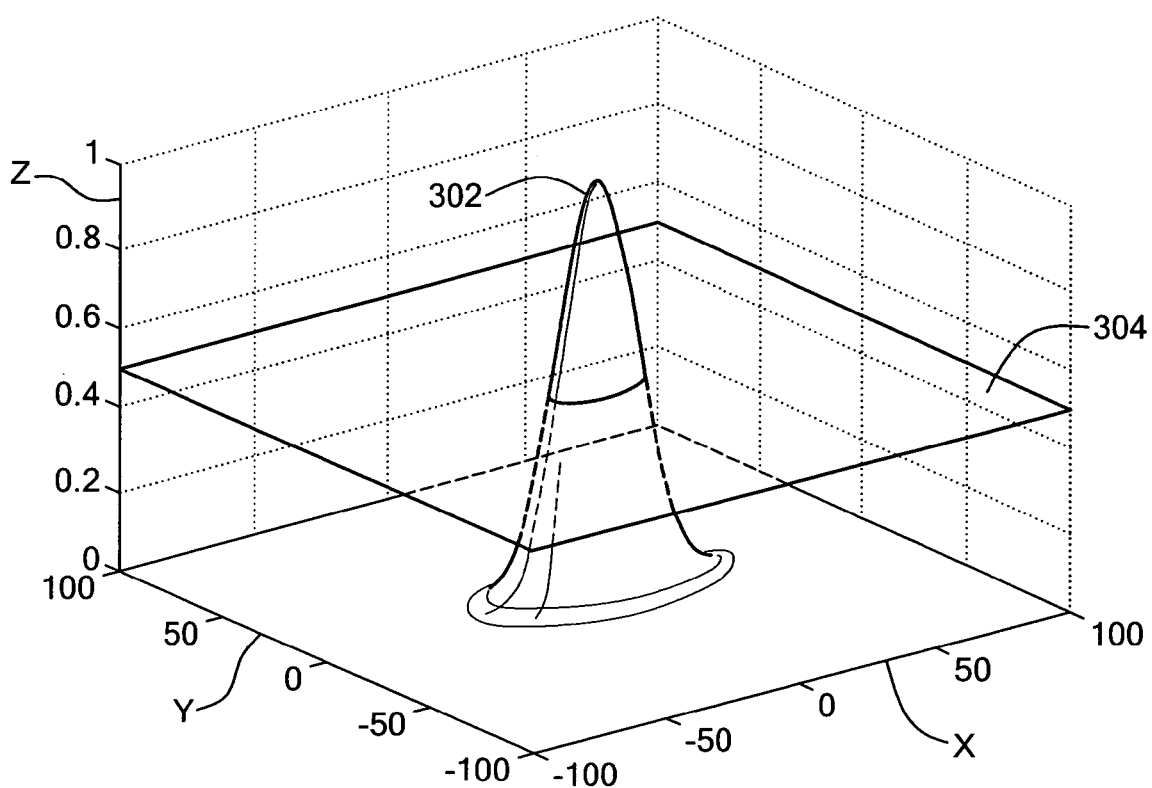
FIG. 3 is a diagram of a first geometric Gaussian shape in three-dimensional space, the first Gaussian shape representing non-saturated data collected by the surface scanning inspection system of FIG. 1.
Figure 4:
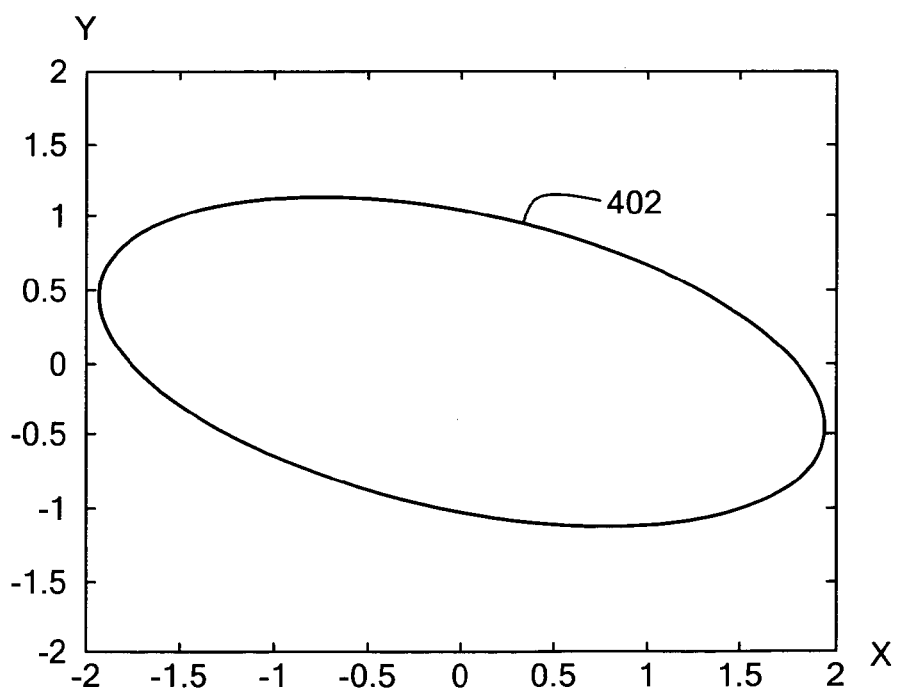
FIG. 4 is a diagram of an elliptical cross-sectional area of the first Gaussian shape of FIG. 3, the cross-sectional area being obtained by conceptually cutting the first Gaussian shape in an x-y plane corresponding to a predetermined height of the Gaussian shape.

The presently disclosed technique will be better understood by reference to the following analysis. FIG. 3 depicts a geometric Gaussian shape 302 in a space defined by x, y, and z axes, in which the Gaussian shape 302 represents non-saturated data collected by the surface scanning inspection system 100 (see FIG. 1). If the Gaussian shape 302 is conceptually cut by an x-y plane 304 at a predetermined amplitude ("cut height") along the z-axis, then the resulting cross-sectional area of the Gaussian shape 302 in the x-y plane 304 has the shape of an ellipse 402 (see FIG. 4). The area of the ellipse 402 may be determined by solving for the area of a region defined by $$\text{power}(\vec{z}) > \text{height}, \tag{8}$$

in which "power($\vec{z}$)" is expressed as indicated in equation (3) above. Substituting this expression for power($\vec{z}$) in equation (8) yields $$(\vec{z} - \vec{z}_0)' R^{-1} (\vec{z} - \vec{z}_0) < \ln(P_0) - \ln(\text{height}). \tag{9}$$

Let $$\text{Area} = \int\int_{(\vec{z}-\vec{z}_0)' R^{-1}(\vec{z}-\vec{z}_0) < \ln(P_0) - \ln(\text{height})} dz, \tag{10}$$

and $$y = R^{-\frac{1}{2}}(\vec{z} - \vec{z}_0), \tag{11}$$

$$dy = |R|^{-\frac{1}{2}} dz,$$

$$dz = |R|^{\frac{1}{2}} dy.$$

Accordingly, $$\text{Area} = \int\int_{|y| < \sqrt{\ln(P_0) - \ln(\text{height})}} |R|^{\frac{1}{2}} dy, \tag{12}$$

$$\text{Area} = \int_0^{2\pi} \int^{\sqrt{\ln(P_0)-\ln(\text{height})}} |R|^{\frac{1}{2}} r dr d\theta, \text{ and} \tag{13}$$

$$\text{Area} = \pi |R|^{\frac{1}{2}} (\ln(P_0) - \ln(\text{height})). \tag{14}$$

Equation (14) above shows that the area of a geometric Gaussian shape conceptually cut at a predetermined height (e.g., the area of the ellipse 402; see FIG. 4) is a linear function of the natural logarithm (ln) of the predetermined cut height. As indicated by equation (14), the cross-sectional area is equal to zero when the cut height equals the scattering power $P_0$ of the defect. Further, the slope of the line defined by equation (14) is equal to $$\pi |R|^{1/2}, \tag{15}$$

in which "$|R|^{1/2}$" is the square root of the determinant of the positive definite symmetric matrix describing the beam shape. It is noted that "$\pi |R|^{1/2}$" is equal to the "1/e" area of the Gaussian shape. Accordingly, after plotting the area values as a function of the natural logarithm (ln) of the predetermined cut heights, and applying a least squares fit to the plot to form a linear plot, the intercept at which the area is zero is equal to the natural logarithm of the scattering power $P_0$, and the slope of the linear plot is equal to the 1/e area of the Gaussian shape.

Figure 5:
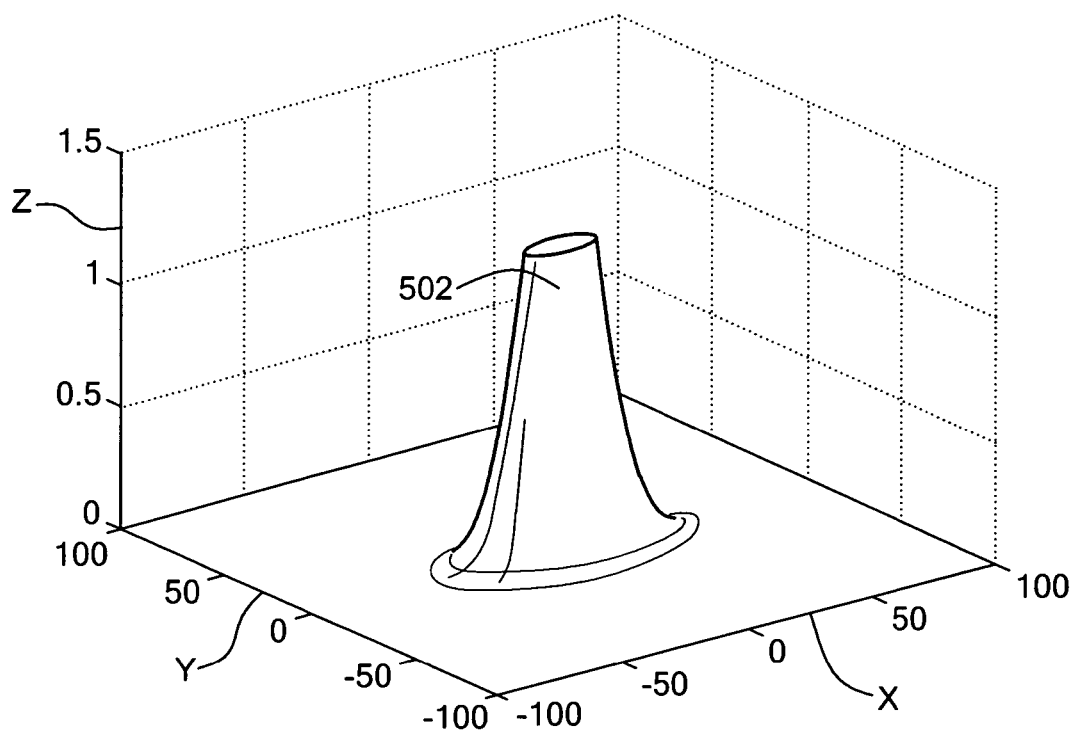
FIG. 5 is a diagram of a second geometric Gaussian shape in three-dimensional space, the second Gaussian shape representing saturated data collected by the surface scanning inspection system of FIG. 1.
Figure 6:
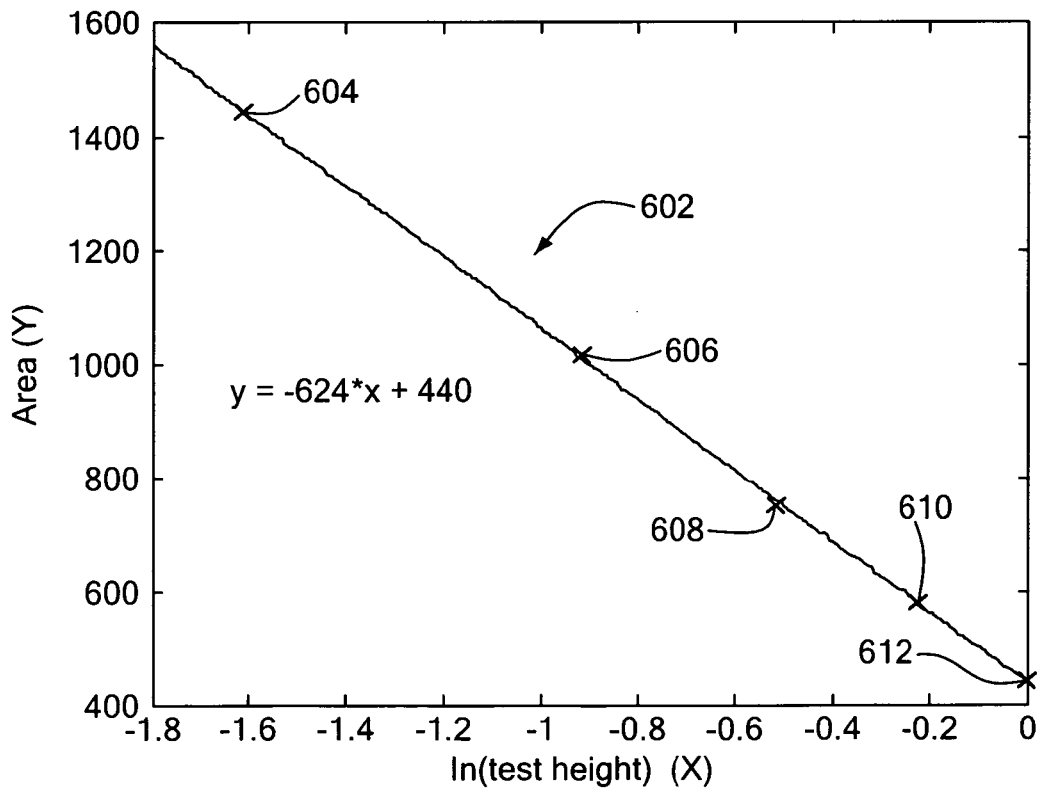
FIG. 6 is a diagram illustrating a linear least squares fit of the data represented by the second Gaussian shape of FIG. 5.

The presently disclosed technique for measuring the size and determining the location of a defect on a semiconductor wafer surface is illustrated by the following example. FIG. 5 depicts a geometric Gaussian shape 502 in x, y, z coordinate space, in which the Gaussian shape 502 comprises saturated data collected by the surface scanning inspection system 100 (see FIG. 1). In this example, the Gaussian shape 502 is conceptually cut in the x-y plane at a plurality of predetermined cut heights along the z-axis, namely, at cut heights of 0.2, 0.4, 0.6, 0.8, and 1.0 units. Next, the respective cross-sectional areas of the Gaussian shape 502 conceptually cut at these predetermined heights are determined. The values of the cross-sectional areas are then plotted versus the natural logarithm (ln) of the respective cut heights, and a least squares fit is applied to the plot to produce a linear plot 602 of the collected data, as depicted in FIG. 6. As shown in FIG. 6, the linear plot 602 includes the data points 604, 606, 608, 610, and 612 corresponding to the predetermined cut heights 0.2, 0.4, 0.6, 0.8, and 1.0, respectively. In this illustrative example, the linear plot 602 may be expressed as $$y = -624x + 440, \tag{16}$$

in which the variable "y" represents the cross-sectional area of the Gaussian shape 502 and the variable "x" represents the natural logarithm of the predetermined cut height.

Accordingly, equation (16) above indicates that the cross-sectional area (y) is equal to zero when the natural logarithm of the cut height (x) equals about 0.705. The cut height at which the cross-sectional area equals zero may therefore be obtained by taking the inverse natural logarithm of 0.705, which is about 2.02. Because the cross-sectional area is equal to zero when the cut height equals the scattering power $P_0$ of a wafer surface defect, as indicated in equation (14) above, $P_0$ is equal to about 2.02. In this example, the actual height of the illustrative Gaussian shape 502 (i.e., the height that would be observed in the absence of saturation effects) is 2.0. Further, the slope of the linear plot 602, as expressed by equation (16) above, is equal to −624, which is the 1/e area of the Gaussian shape. In this example, the actual 1/e area of the Gaussian shape 502 (i.e., the 1/e area that would be observed in the absence of saturation effects) is 200π, or about 628. Based on these results, a correlation coefficient may be calculated as 0.9999. In general, if the correlation coefficient is much less than unity, then the linear least squares fit is considered to be poor. Because the correlation coefficient is equal to 0.9999 in this illustrative example, the linear least square fit is consider to provide an accurate measure of the actual height of the Gaussian shape 502.

The above-discussed methodology extends the linear dynamic range of the wafer scanning system by factor of approximately ten in the optical power domain. By using techniques that involve curve fitting and knowledge of the beam shape, the methodology permits determination of a voltage equivalent magnitude of a defect. With the calculated voltage magnitude, optical models may be used to convert the voltage equivalent magnitude to a scattered power, and then to defect size.

However, the above-described methodology begins to degrade in performance when applied to extend the linear dynamic range of the system beyond the factor of ten. For example, in the range of approximately 50 volts for a voltage equivalent magnitude, the larger defects prevent the beam from accurately retaining a Gaussian shape. That is, as the observed defect becomes larger in size, the outlying lower-power sections of the beam influence the curve fit estimations and averages. Because the optics are not perfect, the beam is not perfectly Gaussian, and the imperfections can degrade the accuracy of the above methodology in the case of very large defects.

Other techniques have been used to detect and measure very large defects that produce pulses outside the dynamic range of the equipment. To measure the very large defects, a cross-sectional area of a Gaussian pulse generated by the defect is determined, based on a given set point threshold, or height for the cross-sectional area. While the results of this technique are fairly robust, an empirical calibration is made between the area of the cross-section and the particle size. That is, a completely separate calibration process is used to set up the measurement, since the nature of the very large defect dramatically increases the range of extrapolation for determining pulse height and thus defect sizing. When the correlation coefficient of the previously described methodology is much less than unity, meaning that a very large defect is detected that introduces some nonlinearly into the methodology, the linear least squares fit is considered to be poor. The impact on the methodology can be observed by visualizing the truncated pulse of FIG. 5 as approaching the shape of a column, indicating a very high pulse, as well as an ill-conditioned fit for the linear relationship used to determine pulse height. In these circumstances, the techniques of the two different methodologies described above can be combined to produce a uniform method for sizing defects over the entire wafer, directly from voltage magnitude calculations, without a completely separate calibration process for the large size defects.

A method according to the present invention involves calculating a cross sectional area at a predetermined threshold of the pulse resulting from a very large defect. A slope value m that is representative of a relationship between the area of a cross-section in a Gaussian pulse and the height of the pulse at the cross-section is then calculated, either as a measured slope value M from the linear least squares fit from previously detected, smaller defects with a good correlation coefficient, or as a system slope value M, from the simple observation that the slope is a function of the beam geometry which does not change from defect to defect. Beam geometry, or spot size, can be measured according to a number of techniques, for example through the use of commercially available apparatus that precisely measures beam spot size. Given that the spot size is proportional to the slope of a relationship between a cross-sectional area and a predetermined cut height, the system slope value M can be calculated from known beam geometry in accordance with the equation $$M = \pi |R|^{\frac{1}{2}}$$

As noted previously, the slope value m can be used in combination with the single cross sectional area and height that are determined within the dynamic range of the equipment to produce an estimate for the pulse height and thus defect size. The cross sectional area in the dynamic range in relation to a height of the cross section is given by the equation.

Area=Ln(voltage amplitude)$m$–Ln(threshold)$m$

Where m is the slope value, area is the cross sectional area of a Gaussian pulse, voltage amplitude is the equivalent voltage magnitude of the area of the Gaussian pulse over the threshold, and threshold is the height of the cross-sectional area in terms of voltage equivalence. Revising the above equation to solve for amplitude gives the expression Voltage amplitude=threshold*$e^{(area/m)}$ which provides a direct method of obtaining an equivalent voltage for the defect.

A method of operating the presently disclosed surface scanning inspection system to determine the amplitude (height) and the 1/e area of a Gaussian shape is illustrated with reference to FIG. 7. It is understood that the height of the Gaussian shape corresponds to the height of a defect detected on a semiconductor wafer surface, and the 1/e area of the Gaussian shape corresponds to the area of a surface scanning laser beam emitted by the wafer inspection system. As depicted in step 702, the wafer inspection system collects a plurality of data samples and analyzes the data samples to detect a defect on the semiconductor wafer surface. It is noted that the data samples, which may comprise saturated data, may be diagrammatically represented by a geometric Gaussian shape. Next, a plurality of predetermined cut heights is determined, as depicted in step 704, for use in conceptually cutting the Gaussian shape to obtain a plurality of corresponding cross-sectional areas of the Gaussian shape. In an embodiment, the plurality of predetermined cut heights includes about 10 height values, ranging from about 20% to about 80% of the maximum height of the Gaussian shape, as indicated by the collected data samples. Relatively small cut height values are preferably omitted to avoid noise effects. For each predetermined cut height, the corresponding cross-sectional area of the Gaussian shape is determined, as depicted in step 706. In the illustrative but not necessarily preferred embodiment, the cross-sectional areas are determined by counting the number of data values that exceed the predetermined cut height, and then multiplying the counted number of data values by the effective area of each value. For example, a useful approximation of the effective cross-sectional area may be obtained by calculating the product of (1) the radial in scan pixel pitch, (2) the tangential cross scan pixel pitch, and (3) the cosine of the boom tilt, which is defined as π/2 radians minus the angle between the in scan and cross scan directions. Next, a linear least squares fit of the data is performed, as depicted in step 708, to obtain a linear plot of the data. For example, in a mathematical expression of the linear plot, the variable "x" corresponds to the natural logarithm (ln) of the predetermined cut heights, and the variable "y" corresponds to the determined cross-sectional areas of the Gaussian shape, and the measured slope value M for the slope of the linear relationship between the natural logarithm (ln) of the height of a Gaussian shape and the cross-sectional areas of the Gaussian shape. A validity test of the regression is then performed, as depicted in step 710, to generate correlation coefficient. If the correlation coefficient value is close to unity, then the above-described method may be employed to provide an accurate measure of the height of the detected defect. However, if the correlation coefficient value is not close to unity, where it varies by more than several percent, or where the. measured slope value M is greater than or less than an acceptable range around the measured slope value M, the detected defect is considered to be too large for the above-described method to produce an accurate measure, and the method according to the present invention is employed.

In step 712, a predetermined cut height or threshold is employed to obtain a cross sectional area of the Gaussian shape. The predetermined cut height or threshold may be one of the plurality determined in step 704, for example, or it may be selected independently of the plurality determined in step 704. The cross sectional area for the predetermined cut height or threshold is determined in step 714. The cross sectional area at the predetermined cut height may be determined according the techniques discussed above, as is done in step 706.

Once the cross sectional area at the predetermined cut height is known, these values are combined with a slope value m, which could comprise system slope value M or measured slope value M, to produce the voltage equivalent magnitude of the defect according to the previously described relationship.

Figure 7:
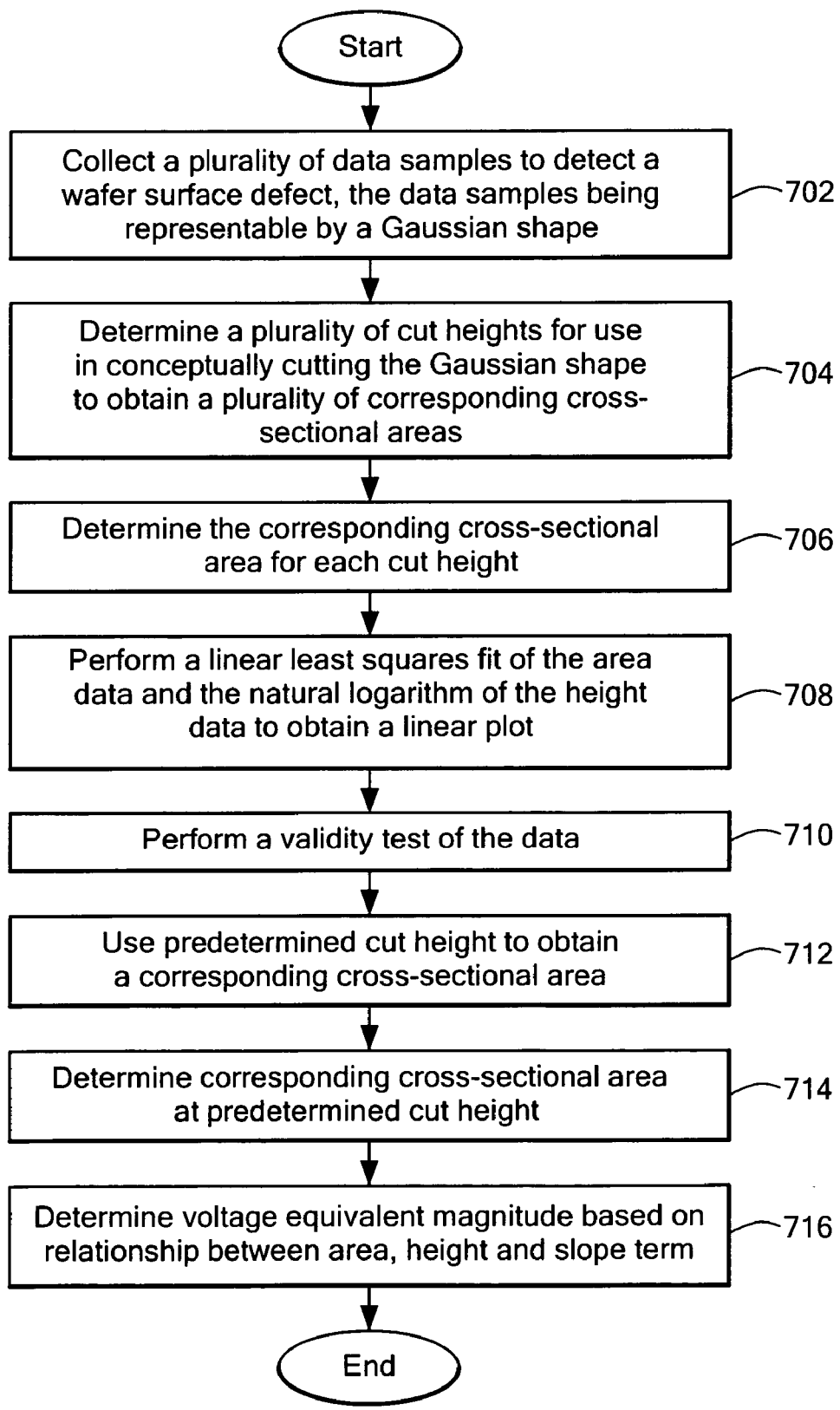
FIG. 7 is a flow diagram of a method of operating the surface scanning inspection system of FIG. 1.

The steps according to the technique in FIG. 7 can be executed rapidly, and can be achieved from the results of data samples based on a single scan of the wafer surface. Accordingly, the present invention provides a significant increase in the available dynamic range of the system, by several orders of magnitude to approximately 1,000 volts. The equivalent voltage measured in accordance to the technique of the present invention can be used with theoretical models or empirical calibration to size defects directly. According to an exemplary embodiment of the present invention, the predetermined voltage used to define the cut height for obtaining the cross-sectional area of the Gaussian shape is set to 2.7 volts. This setting provides a threshold height within the range of the equipment for accurate measurement of the cross-sectional area with less influence from noise. It is noted that the determined area of the surface scanning laser beam may be employed by the wafer inspection system as a diagnostic measure.

An advantage of the present invention is that it provides an inspection system and method that extends the linear dynamic range of an inspection system by greater than a factor of ten over prior laser inspection systems in the optical power domain. The first methodology, which uses curve fitting and knowledge of the beam shape to determine the voltage equivalent magnitude of a defect, extends the linear dynamic range of the inspection system by a factor of approximately ten over prior laser inspection systems in the optical power domain. However, it begins to degrade in performance beyond a factor of approximately 10-50 Volts, because it relies upon the beam accurately retaining a Gaussian shape. As the defects become larger, the outlying lower-power sections of the beam have a greater influence on the curve fit. Since the optics are not perfect, the beam is not perfectly Gaussian. These imperfections tend to degrade the accuracy of the methodology.

The incorporation of a second methodology into the system, in which the voltage equivalent magnitude of a defect is determined by combining the slope value, a predetermined voltage threshold, and an estimate of a defect area at the predetermined voltage threshold, extends the linear dynamic range of the inspection system beyond the factor of ten over prior laser inspection systems in the optical power domain.

Having described the above illustrative embodiments, other alternative embodiments or variations may be made. For example, it was described that a linear least squares fit may be employed for fitting the cross-sectional areas to the natural logarithms of the predetermined cut heights. However, such linear least squares fitting was described for purposes of illustration, and other techniques may be employed, including a polynomial fit, a nonlinear least squares fit, or a noise weighted least squares fit technique.

It will be appreciated by those of ordinary skill in the art that further modifications to and variations of the above-described extended defect sizing technique may be made without departing from the inventive concepts disclosed herein. Accordingly, the invention should not be viewed as limited except as by the scope and spirit of the appended claims.

What is claimed is:

1. A method for determining a size of a defect on a semiconductor wafer when subjected to a surface scanning laser beam to produce data samples that can be used to represent a geometric Gaussian shape in three dimensional space, the defect size being related to a height of the Gaussian shape, the method comprising:

defining a cross-sectional area of the Gaussian shape corresponding to an intermediate height of the Gaussian shape;
determining a value of the cross-sectional area;
obtaining a slope value that is representative of a relationship between the cross-sectional area and the intermediate height;
combining the intermediate height, cross-sectional area value and a slope value in a given relationship to produce a height projection of the Gaussian shape, the height projection being an equivalent voltage magnitude representative of the defect size; and
sizing the defect based on the equivalent voltage magnitude.

2. The method according to claim 1, further comprising determining the slope value from prior defect measurements.

3. The method according to claim 1, further comprising:
applying a first sizing technique to determine an estimated height of the Gaussian shape;
performing a validity analysis to determine validity of the estimated height; and
implementing an additional height determination in dependence on results of the validity analysis.

4. The method in accordance with claim 3, wherein said additional height determination comprises said method for determining the size of the defect.

5. The method according to claim 1, further comprising:
determining the cross-sectional area value as a function of the natural logarithm of the intermediate height value substantially in accordance with the equation $$\text{Area} = \pi |R|^{\frac{1}{2}} (\ln(P_0) - \ln(\text{height})),$$

wherein "$P_0$" is a maximum scattering power associated with the detected defect, and "R" is a positive definite symmetric matrix describing a shape associated with a laser beam used to generate the Gaussian shape.

6. The method according to claim 1, further comprising determining a height of a plurality of Gaussian shapes representative of defect sizes on a wafer with a single scan of a beam used to generate the Gaussian shapes.

7. The method according to claim 1, wherein the equivalent voltage magnitude representative of the defect size comprises a value representative of voltage or power amplitude for the Gaussian shape, and the given relationship further comprises $$\text{Amplitude} = \text{height} * e^{(area/m)}$$

where height is the intermediate height, area is the cross-sectional area value and m is the slope value.

8. The method according to claim 7, wherein the height determination provides an increase of a dynamic range of an associated system of an order of magnitude or more.

9. A system for determining a height of a geometric Gaussian shape in three dimensional space that is representative of a defect size on a wafer, comprising:
a data capture component for capturing data samples related to scattering power of an incident beam on a surface of the wafer;
a processing engine for executing a set of instructions for analyzing the data samples and determining the height; and
the set of instructions being configured to determine the height when the Gaussian shape exceeds a dynamic range of the equipment and determine a size of a defect corresponding to the Gaussian shape based on the height.

10. The system according to claim 9, wherein the set of instructions is configured to be executable by the processing engine to determine a value representative of voltage or power amplitude substantially according to the equation Amplitude=height*$e^{(area/m)}$ where height is the intermediate height, area is the cross-sectional area value and m is a slope value that is representative of a relationship between an area of a cross-section in a Gaussian pulse and a height of the pulse at the cross-section.

11. A method for determining a size of a defect on a wafer, comprising:
    determining a shape height of a geometric Gaussian shape in three dimensional space that is representative of the defect size by:
        defining an intermediate height of the Gaussian shape;
        defining an intermediate cross-sectional area of the Gaussian shape corresponding to the intermediate height;
        determining a value for the intermediate cross-sectional area; and
        determining a slope value related to slope of a linear relationship between area of a cross-section in a Gaussian pulse and the natural log of height of the cross-section;
    combining the intermediate height, the intermediate cross-sectional area value, and the slope value in a given relationship to produce an equivalent voltage magnitude representative of the defect size; and
    sizing the defect based on the equivalent voltage magnitude.

12. The method of claim 11, wherein the equivalent voltage magnitude comprises a height amplitude for the Gaussian shape, and wherein the given relationship further comprises Amplitude=height*$e^{(area/m)}$ where height is the intermediate height, area is the intermediate cross-sectional area value, and m is the slope value.

13. The method of claim 11, further comprising using a defect inspection system to determine detect size, and wherein said slope value comprises a system slope value M that is based on known characteristics of said defect inspection system.

14. The method of claim 13, wherein said system slope value is derived substantially in accordance with the equation $$M = \pi |R|^{\frac{1}{2}},$$

where R is a positive definite symmetric matrix describing a shape associated with a laser beam in said defect inspection system.

15. A method for determining a size of a defect on a water by determining a shape height of a geometric Gaussian shape in three dimensional space that is representative of the defect size, comprising:
    determining said shape height using a plurality of cross-sections of the Gaussian shape, further comprising:
        using a shape of a beam directed at the wafer and curve fitting techniques to determine a voltage or power equivalent magnitude of a defect from said plurality of cross-sections, said techniques comprising determining a slope value for a slope that is representative of a relationship between an area of a cross-section in a Gaussian pulse and a height of the pulse at the cross-section;
    performing a validity analysis to determine the validity of the voltage or power equivalent magnitude of a defect from said plurality of cross-sections;
    when the validity analysis demonstrates invalidity of the voltage or power equivalent magnitude, determining the shape height using height projection, further comprising
        defining a cross-sectional area of the Gaussian shape corresponding to an intermediate height;
        determining a value for the cross-sectional area;
        combining the intermediate height, cross-sectional area value and the slope value in a given relationship to produce an equivalent voltage magnitude representative of the defect size; and
    sizing the defect based on the equivalent voltage magnitude.

16. A method of inspecting a semiconductor wafer for determining size and location of wafer defects by developing an equivalent voltage or power value for a defect related to defect size, comprising:
    using a first defect size estimation technique to size defects over a first defect size range, and
    using a second defect size estimation technique to size defects over a second defect size range being greater than the first defect size range, wherein using said second defect size estimation technique further comprises using information obtained from said first defect size estimation technique for predicting said defect size.

17. The method of claim 16, further comprising directing an incident beam onto a surface of the semiconductor wafer;
    wherein using said first defect size estimation technique further comprises obtaining a plurality of cross-sections of a Gaussian shape representative of said defect, and employing curve fitting and knowledge of the shape of the incident beam on the defect to determine the voltage equivalent magnitude of said defect,
    and wherein using the second defect size estimation technique further comprises determining the voltage equivalent magnitude of a defect by combining a slope value representative of a relationship between the area of a cross-section in a Gaussian pulse and a height of the pulse at the cross-section, a predetermined voltage threshold, and an estimate of a defect area at the predetermined voltage threshold.

18. The method of claim 16, wherein said information further comprises a slope value representative of a relationship between the area of a cross-section in a Gaussian pulse and a height of the pulse at the cross-section.

* * * * *

UNITED STATES PATENT AND TRADEMARK OFFICE
CERTIFICATE OF CORRECTION

| | | |
|---|---|---|
| PATENT NO. | : 7,302,360 B2 | Page 1 of 1 |
| APPLICATION NO. | : 11/321689 | |
| DATED | : November 27, 2007 | |
| INVENTOR(S) | : Neil Judell | |

It is certified that error appears in the above-identified patent and that said Letters Patent is hereby corrected as shown below:

Column 3, line 25, "processobtains" should read --process obtains--; and

Column 15, claim 15, line 59, "on a water" should read --on a wafer--.

Signed and Sealed this

Fourth Day of November, 2008

JON W. DUDAS
*Director of the United States Patent and Trademark Office*